United States Patent
Wang et al.

(10) Patent No.: US 11,850,429 B2
(45) Date of Patent: Dec. 26, 2023

(54) MULTI-TARGET ELECTRICAL STIMULATION CIRCUIT, ELECTRICAL STIMULATOR AND SIGNAL OUTPUT METHOD OF ELECTRICAL STIMULATOR

(71) Applicant: Xuanwu Hospital Capital Medical University, Beijing (CN)

(72) Inventors: Yuping Wang, Beijing (CN); Zhiyuan Yan, Beijing (CN)

(73) Assignee: Xuanwu Hospital Capital Medical University, Beijing (CN)

( * ) Notice: Subject to any disclaimer, the term of this patent is extended or adjusted under 35 U.S.C. 154(b) by 44 days.

(21) Appl. No.: 17/759,993

(22) PCT Filed: Apr. 3, 2020

(86) PCT No.: PCT/CN2020/083321
§ 371 (c)(1),
(2) Date: Aug. 2, 2022

(87) PCT Pub. No.: WO2021/184439
PCT Pub. Date: Sep. 23, 2021

(65) Prior Publication Data
US 2023/0065138 A1    Mar. 2, 2023

(30) Foreign Application Priority Data

Mar. 16, 2020    (CN) ......................... 202010179227.2

(51) Int. Cl.
*A61N 1/36* (2006.01)
*A61N 1/02* (2006.01)

(52) U.S. Cl.
CPC ......... *A61N 1/36192* (2013.01); *A61N 1/025* (2013.01); *A61N 1/36139* (2013.01); *A61N 1/36064* (2013.01)

(58) Field of Classification Search
CPC ............... A61N 1/025; A61N 1/36064; A61N 1/36139; A61N 1/36192
See application file for complete search history.

(56) References Cited

U.S. PATENT DOCUMENTS

| | | | |
|---|---|---|---|
| 8,938,291 | B1 | 1/2015 | Azarnasab et al. |
| 10,583,294 | B2 | 3/2020 | De Ridder |

(Continued)

FOREIGN PATENT DOCUMENTS

| | | | |
|---|---|---|---|
| CN | 102149428 | A | 8/2011 |
| CN | 102480352 | A | 5/2012 |

(Continued)

OTHER PUBLICATIONS

China National Intellectual Property Administration (ISA/CN), International Search Report for PCT/CN2020/083321, dated Dec. 14, 2020, 5 pages.

(Continued)

*Primary Examiner* — Amanda K Hulbert
(74) *Attorney, Agent, or Firm* — Jaffery Watson Mendonsa & Hamilton LLP (57) ABSTRACT

The present invention relates to a multi-target electrical stimulation circuit, an electrical stimulator, and a signal output method of the electrical stimulator. The electrical stimulation circuit includes a control module, a plurality of brain wave acquisition modules and a plurality of stimulation adjustment modules. Each electrode is correspondingly provided with one brain wave acquisition module and one stimulation adjustment module, and different electrodes are used for stimulating different targets. The brain wave acquisition modules are used for acquiring brain wave signals in the corresponding electrodes and transmitting the brain wave signals to the control module. The control module is used for acquiring brain rhythm phase signals according to the received brain wave signals and outputting stimulation (Continued)

signals at preset waveform phase points after phase locking of the brain rhythm phase signals. The stimulation adjustment modules are used for adjusting brain wave stimulation signals output to the corresponding electrodes according to the received stimulation signals. The multi-target electrical stimulation circuit, the electrical stimulator and the signal output method provided by the present invention are beneficial for achieving electrical stimulation of a plurality of targets as well as time-locked matching of electrical stimulation of a plurality of targets.

12 Claims, 4 Drawing Sheets

(56) References Cited

U.S. PATENT DOCUMENTS

| 2003/0233050 A1 | 12/2003 | Haghighi-Mood et al. |
| 2016/0220836 A1 | 8/2016 | Parks |
| 2016/0331441 A1 | 11/2016 | Konings |
| 2019/0059803 A1 | 2/2019 | Myers et al. |

FOREIGN PATENT DOCUMENTS

| CN | 105122246 A | 12/2015 |
| CN | 205252313 U | 5/2016 |
| CN | 108744273 A | 11/2018 |
| CN | 109173047 A | 1/2019 |
| CN | 109603006 A | 4/2019 |
| CN | 110101385 A | 8/2019 |
| CN | 110548226 A | 12/2019 |
| CN | 110812693 A | 2/2020 |
| EP | 2821103 A1 | 1/2015 |

OTHER PUBLICATIONS

D'Amato, Giulio et al., "An Integrated Phase Shifting Frequency Synthesizer for Active Electronically Scanned Arrays," Apr. 2018, www.researchgate.net/publication/326365228, 5 pages.

The State Intellectual Property Office of People's Republic of China, First Office Action for Chinese Patent Application No. 202010179227.2, dated Aug. 19, 2020, 25 pages.

The State Intellectual Property Office of People's Republic of China, Second Office Action for Chinese Patent Application No. 202010179227.2, dated Dec. 7, 2020, 22 pages.

MULTI-TARGET ELECTRICAL STIMULATION CIRCUIT, ELECTRICAL STIMULATOR AND SIGNAL OUTPUT METHOD OF ELECTRICAL STIMULATOR

CROSS-REFERENCE TO RELATED APPLICATIONS

This application is a national phase application of International Application No. PCT/CN2020/083321, filed on Apr. 3, 2020, which claims the benefits of Chinese Patent Application No. 202010179227.2, filed on Mar. 16, 2020, each of which is hereby incorporated by reference in its entirety.

The present application claims the priority of the Chinese Patent Application No. 202010179227.2, filed to China Patent Office on Mar. 16, 2020, entitled "Multi-Target Electrical Stimulation Circuit, Electrical Stimulator and Signal Output Method of Electrical Stimulator," the entire contents of which are incorporated herein by reference.

TECHNICAL FIELD

The present application relates to the technical field of medical devices, and in particular to a multi-target electrical stimulation circuit, an electrical stimulator, and a signal output method of the electrical stimulator.

BACKGROUND

In recent years, with the development of neuroimaging technology, the improvement of brain signal analysis methods and the breakthrough of medical concepts, some brain diseases show new common features in pathogenesis and therapies, and new disease groups are gradually formed, which are referred to as brain functional diseases. This kind of disease has abnormal brain network features, which can be regulated by electrical stimulations, so that the abnormal brain network features and clinical symptoms can be changed. The concept of functional brain diseases has opened up a new field of clinical diagnosis and treatment and brought hope for brain diseases, which have been difficult to diagnose and treat for a long time.

Increasing evidence of neural electrophysiology and imageology research show that there are brain network abnormalities in nervous system related functional brain diseases, involving a plurality of neural circuits among which there are interactions. For example, abnormal brain networks closely related to pathogenesis of depression include emotional loops and reward loops. In the case of Alzheimer's disease, memory and execution control networks are closely related to cognitive and behavioral disorders of Alzheimer's patients. In each disease, all neural circuits have an interaction adjustment effect on one another and affect one another. Therefore, abnormal networks of a whole brain in a disease state cannot be adjusted by electrically stimulating a key brain region of only a certain neural circuit, which limits the therapeutic effect.

According to an existing brain stimulation technology adopting a Responsive Neurostimulation System (RNS), a depth electrode is implanted in an epileptic focus of a human brain, and the depth electrode can acquire intracranial electrical signals and can also provide electrical stimulation to brain regions. The RNS can continuously monitor brain wave signals and recognize epileptic discharge in real-time and implements electrical stimulation in time when an epileptic occurs or is going to trigger an epileptic seizure to stop the development of the epileptic discharge, and thus the epileptic seizure can be prevented. However, the RNS can only achieve electrical stimulation of two targets at most, namely electrical stimulation of two key brain regions, but cannot achieve whole brain regulation of functional brain diseases of a plurality of neural circuits. Moreover, time-locked matching cannot be achieved in the stimulation of two targets. That is, the two targets cannot be stimulated synchronously or sequentially at fixed time intervals.

SUMMARY

The present application aims to solve the technical problems that abnormal networks of a whole brain in a disease state cannot be adjusted by electrically stimulating a key brain region of only a certain neural circuit and that time-locked matching of stimulation of two targets cannot be achieved. That is, two targets cannot be stimulated simultaneously or at preset time intervals.

To solve the above technical problems, in a first aspect, an embodiment of the present application provides a multi-target electrical stimulation circuit, including:

a control module, a plurality of brain acquisition modules, and a plurality of stimulation adjustment modules, where each electrode is configured with a corresponding brain wave acquisition module and a corresponding stimulation adjustment module, and where different electrodes are used to simulate different targets.

The brain wave acquisition modules are configured to acquire brain wave signals in the corresponding electrodes and transmitting the brain wave signals to the control module.

The control module is configured to obtain brain rhythm phase signals according to the received brain wave signals and output stimulation signals at preset waveform phase points after phase locking of the brain rhythm phase signals.

The stimulation adjustment modules are configured to adjust brain wave stimulation signals output to the corresponding electrodes according to the received stimulation signals.

Optionally, the control module may include:
a transform submodule for performing a Fourier transform on the received brain wave signals to obtain amplitude spectra and obtaining peak amplitude values according to the amplitude spectra;
a comparison submodule used for comparing the peak amplitude values with threshold amplitude values and adjusting output comparison signals; and
a spectrum analysis submodule for performing FFT phase spectrum analysis on the received brain wave signals according to the received comparison signals to obtain the brain rhythm phase signals.

Optionally, the control module may further include:
a compensation submodule for compensating the brain rhythm phase signals according to acquisition delay parameters and obtaining the compensated brain rhythm phase signals.

Optionally, the control module may further include:
a phase-locking submodule for phase locking of the brain rhythm phase signals and outputting phase-locked brain rhythm phase signals; and
a phase selection submodule for selecting the preset waveform phase points in the phase-locked brain rhythm phase signals and outputting the stimulation signals at the preset waveform phase points.

Optionally, the brain wave acquisition module may include:

an amplification submodule for acquiring brain wave signals in the corresponding electrodes and amplifying the brain wave signals to generate amplified brain wave signals; and an analog-to-digital conversion submodule for converting the amplified brain wave signals in the form of analog signals into amplified brain wave signals in the form of digital signals and transmitting the amplified brain wave signals to the control module.

Optionally, the stimulation adjustment modules are configured to adjust voltages of the received stimulation signals and outputting the voltage-adjusted stimulation signals to the corresponding electrodes.

Optionally, the multi-target electrical stimulation circuit may further include:

a processing module, wherein the processing module is in communication connection with the control module and the stimulation adjustment modules respectively, and wherein the control module sends the stimulation signals to the stimulation adjustment modules through the processing module.

Optionally, the multi-target electrical stimulation circuit may further include:

a wireless charging module and a battery module, wherein the wireless charging module is configured to charge the battery module at preset time intervals, and wherein the battery module is configured to supply power to the processing module, the brain wave acquisition modules, and the stimulation adjustment modules.

In a second aspect, the present application further provides a multi-target electrical stimulation circuit, including the multi-target electrical stimulation circuit according to the first aspect.

In a third aspect, the present application further provides a signal output method of a multi-target electrical stimulator, including:

acquiring brain wave signals in corresponding electrodes and transmitting the brain wave signals to a control module using brain wave acquisition modules, wherein different electrodes are used to simulate different targets, and each electrode is configured with a corresponding brain wave acquisition module;

acquiring brain rhythm phase signals according to the received brain wave signals and outputting stimulation signals at preset waveform phase points after phase locking of the brain rhythm phase signals by using the control module; and adjusting brain wave stimulation signals output to the corresponding electrodes according to the received stimulation signals using stimulation adjustment modules, wherein each electrode is configured with a corresponding stimulation adjustment module.

Compared with the prior art, the above technical solution provided by the embodiments of the present application has the following beneficial effects.

According to the multi-target electrical stimulation circuit provided by the embodiment of the present application, each electrode is configured with a corresponding brain wave acquisition module and a corresponding stimulation adjustment module. Different electrodes are used for stimulating different targets. The brain wave acquisition modules acquire brain wave signals in the corresponding electrodes and transmit the brain wave signals to the control module. The control module obtains the brain rhythm phase signals according to the received brain wave signals and outputs stimulation signals at preset waveform phase points after phase locking of the brain rhythm phase signals. The stimulation adjustment modules adjust brain wave stimulation signals output to the corresponding electrodes according to the received stimulation signals, therefore facilitating the stimulation of a plurality of targets. Accordingly, networks of the whole brain of a brain functional disease of a plurality of neural circuits are adjusted. Meanwhile, feedback type electrical stimulation adjustment of the brain rhythm of a specific objective is achieved by monitoring the brain wave signals in real-time. Furthermore, by phase locking of the brain rhythm phase signals, time-locked matching of electrical stimulation of a plurality of targets is realized. As such, different targets can be stimulated synchronously or stimulated sequentially at preset time intervals.

It should be understood that the above general description and the following detailed description are merely exemplary and explanatory and are not intended to limit the present invention.

BRIEF DESCRIPTION OF THE DRAWINGS

The drawings here, which are incorporated in and constitute a part of the specification, illustrate embodiments consistent with the present application and are intended to explain the principles of the present application together with the specification.

To describe the embodiments of the present application or technical solutions in the prior art more clearly, the drawings required in description of the embodiments or the prior art will be briefly described below. Apparently, some other drawings can also be obtained by those skilled in the art based on these drawings without creative efforts.

DETAILED DESCRIPTION

In order to make the aim, the technical solution and the advantages of the embodiments of the present application clearer, the technical solution of the embodiments of the present application will be described below clearly and completely in conjunction with the drawings in the embodiments of the present application; apparently, the described embodiments are merely part of embodiments of the present application rather than all embodiments. Based on the embodiments in the present application, all other embodiments obtained by those of ordinary skill in the art without making any creative work fall within the protection scope of the present application.

Figure 1:
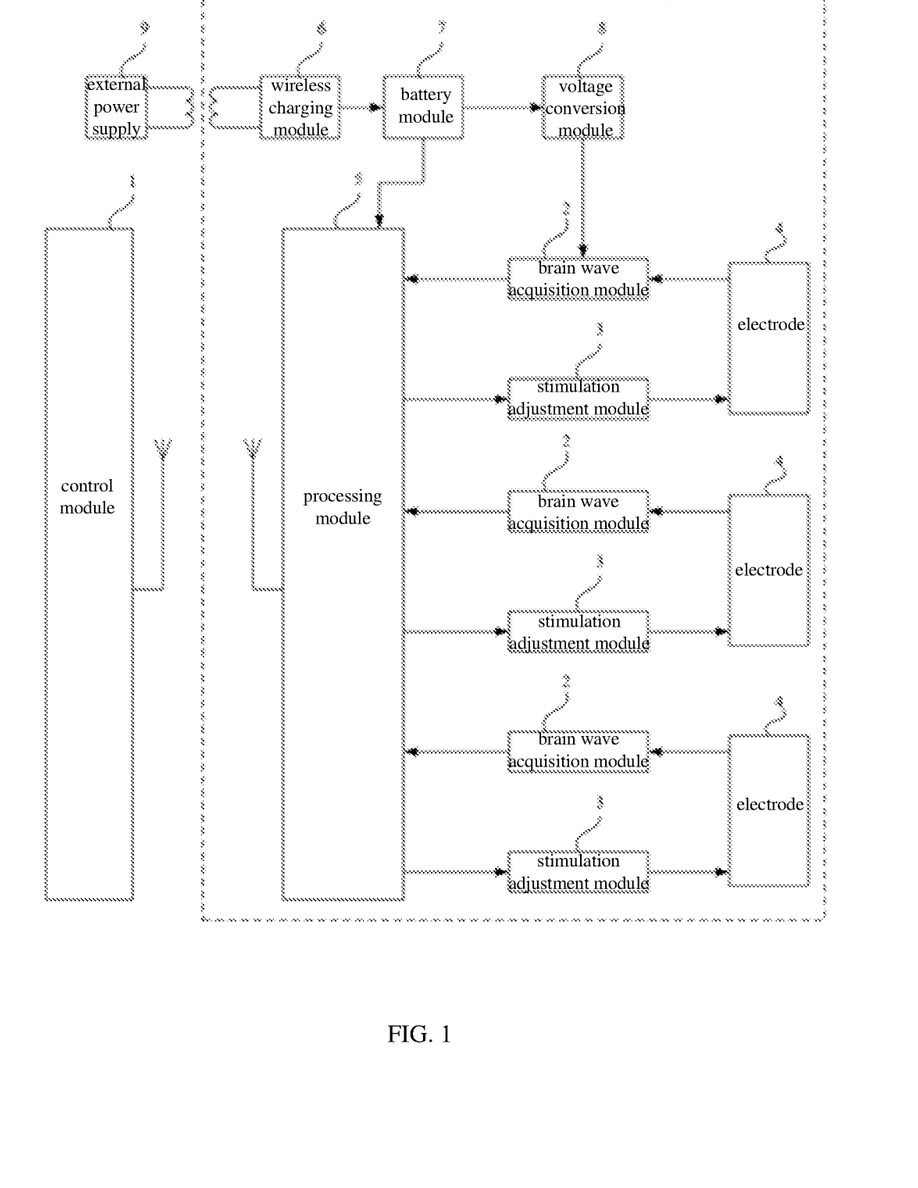
FIG. 1 is a structural schematic diagram of a multi-target electrical stimulation circuit provided by an embodiment of the present invention.

FIG. 1 is a structural schematic diagram of a multi-target electrical stimulation circuit in accordance with an embodiment of the present invention. As shown in FIG. 1, the multi-target electrical stimulation circuit includes a control module 1, a plurality of brain wave acquisition modules 2, and a plurality of stimulation adjustment modules 3. Each electrode 4 is configured with a corresponding brain wave acquisition module 2 and a corresponding stimulation adjustment module 3. As an example, FIG. 1 illustrates three electrodes 4 as well as their corresponding three brain wave acquisition modules 2 and three stimulation adjustment modules 3. An electrical stimulator may include at least three electrodes 4. Different electrodes 4 are used to stimulate different targets, namely key brain regions.

Brain wave acquisition module 2 can acquire a brain wave signal from its corresponding electrode 4 and transmit the brain wave signal to the control module 1. The control module 1 can obtain a brain rhythm phase signal and output a stimulation signal in a set waveform phase point after the brain rhythm phase signal is phase locked. Each stimulation adjustment module 3 can adjust a brain wave stimulation signal according to the received stimulation signal and output the brain wave stimulation signal to the corresponding electrode 4.

Specifically, electrode 4 may be an implanted electrode. That is, electrode 4 is fixed to a preset position in the brain; and the brain wave acquisition modules 2 acquires brain wave signals in the corresponding electrodes 4. As such, the brain wave acquisition modules 2 can monitor the brain wave signals at the preset position in the brain in real-time and transmit the acquired brain wave signals to the control module 1. For example, the multi-target electrical stimulation circuit may further include a processing module 5 which can be in communication connection, such as wireless connection, with the control module 1. The brain wave acquisition modules 2 can transmit the acquired brain wave signals to the control module 1 through the processing module 5.

The control module 1 can receive the brain wave signals transmitted by the brain wave acquisition modules 2, obtain the brain rhythm phase signals according to the brain wave signals to phase lock the brain rhythm phase signals, and output stimulation signals at the preset waveform phase points of the phase-locked brain rhythm phase signals. For example, phase locking can be performed at or after a zero-crossing point of the brain rhythm phase signals for a preset time. Stimulation signals can then be output to phase lock the brain rhythm phase signals. As an example, the multi-target electrical stimulation circuit may further include a processing module 5. Communication connection can be provided. For example, the processing module 5 may be in wireless connection with the control module and in wireless connection or wired connection with the stimulation adjustment modules 3. The control module 1 can send stimulation signals to the stimulation adjustment modules 3 at the preset waveform phase points through the processing module 5 integrated in the body of a patient via wireless communication.

In this way, by virtue of different electrodes 4, time-locked matching of electrical stimulation of a plurality of targets can be effectively achieved by phase locking of the brain rhythm phase signals. That is, different targets can be stimulated synchronously or sequentially at fixed time intervals, which may thus solve the problem that different targets cannot be stimulated synchronously or at fixed time intervals.

In addition, three or more electrodes 4 can be arranged in this embodiment of the present invention, where each electrode 4 is configured with a corresponding brain wave acquisition module 2 and a corresponding stimulation adjustment module 3 to realize multi-target electrical stimulation, thereby achieving whole brain network adjustment of functional brain diseases of a plurality of neural circuits, achieving synchronous adjustment of a plurality of key brain regions of the brain network by fully utilizing the interactive adjustment capability of the plurality of neural circuits, solving the problem that the existing implanted brain stimulation technology can adjust only one or two key brain regions of the brain network, and facilitating the improvement of therapeutic efficacy for functional brain diseases. Meanwhile, according to the embodiment of the present invention, the brain wave signals are monitored in real-time, and electrical stimulation is triggered in real-time according to features of the brain wave signals, so that a specific target brain wave rhythm is subjected to accurate phase-coupled stimulation. In this way, the rhythm of a specific frequency range is adjusted. This may solve the problem that the existing implanted brain stimulation technology cannot achieve stimulation based on its own biological rhythm and may improve brain functional diseases caused by abnormal brain wave rhythm and may further solve the problem that the existing implanted brain stimulation technology can only be used for inhibiting epileptic discharge and may expand the patient population treated by the implanted type brain stimulation technology.

Figure 2:
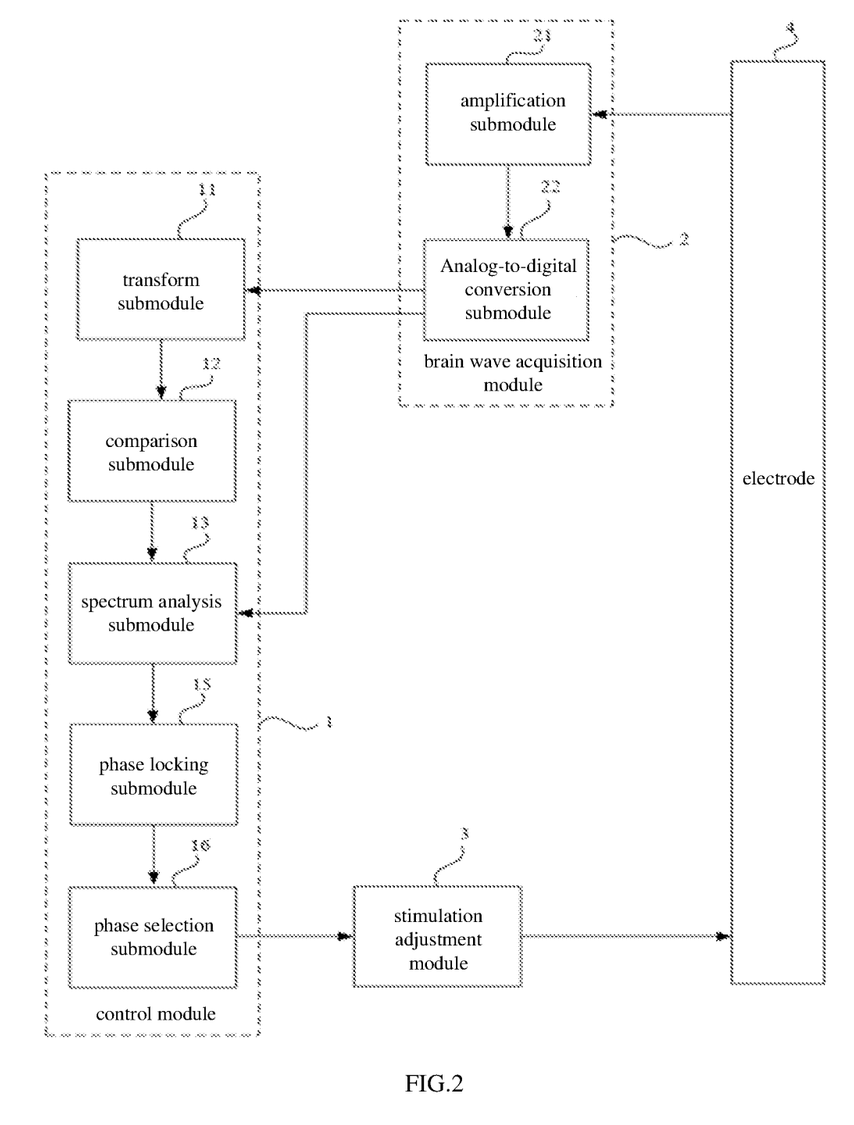
FIG. 2 is a structural schematic diagram of a control module provided by an embodiment of the present invention.

FIG. 2 is a structural schematic diagram of a control module in accordance with the embodiment of the present invention. With reference to FIGS. 1 and 2, based on the above embodiment, the control module 1 may include a transform submodule 11, a comparison submodule 12, and a spectrum analysis submodule 13. The transform submodule 11 may obtain an amplitude spectrum by performing a Fourier transform on the received brain wave signals and may obtain a peak amplitude value according to the amplitude spectrum, where the amplitude spectrum may be an energy amplitude spectrum obtained after the Fourier transform. The comparison submodule 12 may compare the peak amplitude value with a threshold amplitude value and adjust output comparison signals. The spectrum analysis submodule 13s may perform FFT phase spectrum analysis on the received brain wave signals according to the received comparison signals to obtain the brain rhythm phase signals.

Specifically, the brain wave collected by an intracranial electrode 4 is used for monitoring the resting and sleeping brain rhythms of a monitored person in real-time. The brain wave signals acquired by the brain wave acquisition modules 2 are processed using a Fourier transform to obtain amplitude spectra. The amplitude spectra are analyzed in a range from 1 Hz to 30 Hz to monitor amplitude changes of a main frequency range of the brain rhythms. However, when a person is in an abnormal state, the brain wave fluctuates sharply. Therefore, the comparison submodule 12 compares the peak amplitude value obtained by the transform submodule 11 with the threshold amplitude value. The control module 1 outputs an electrical stimulation signal when the peak amplitude value is greater than or equal to the threshold amplitude value.

When the peak amplitude value is greater than or equal to the threshold amplitude value, the spectrum analysis submodule 13 performs FFT (Fast Fourier Transform) phase spectrum analysis on the received brain wave signals according to the received comparison results to obtain brain rhythm phase signals, that is, the comparison submodule 12 monitors biological rhythms according to the peak amplitude value and a set threshold amplitude value, and the spectrum analysis submodule 13 obtains a phase value of a waveform of this rhythm through FFT phase spectrum analysis.

In addition, RNS can only recognize epileptic discharges for electrical stimulation adjustment, but cannot achieve accurate phase-coupled stimulation of other non-epileptic electrical activity types of brain wave, for example, the RNS cannot specifically adjust a delta rhythm in a sleep stage and an alpha rhythm in an awake stage, etc. Functional brain diseases have been found to be related to non-epileptic electrical activity types, such as increase or decrease of normal bioelectrical brain wave rhythms, the degree of phase synchronization of electrical activities of the brain between brain regions, etc. Taking the core feature, namely the work memory defect, of cognitive decline as an example, research show that there is disconnection of the brain network due to the work memory defect, that is, the degree of neural synchronization in frontotemporal cortexes and between the frontotemporal cortexes is obviously weakened. After an electrical stimulation treatment in a frequency range matched with dynamic features of an individual brain network, the results show that there is obviously increased neural synchronization in the frontotemporal cortexes and between the frontotemporal cortexes, and the work memory ability is significantly improved. Therefore, the future electrical stimulation adjustment treatment for functional brain diseases is not merely limited to the electrical stimulation adjustment of epileptic discharge but should be extended to the electrical stimulation adjustment of non-epileptic electrical activity types. The principle of the RNS's recognition on epilepsy is that the RNS continuously monitors the brain wave signals in real-time and recognizes epileptic discharge; when epileptic discharge occurs and is going to trigger an epileptic seizure soon, the RNS implements electrical stimulation in time to stop the development of the epileptic discharge to prevent epileptic seizure.

According to the embodiments of the present invention, the comparison submodule 12 is used for comparing the peak amplitude value obtained by the transform submodule 11 with the threshold amplitude value, and the control module 1 outputs an electrical stimulation signal only when the peak amplitude value is greater than or equal to the threshold amplitude value. That is, according to this embodiment of the present invention, the brain wave signals are monitored in real-time, and the obtained peak amplitude value is continuously compared with the threshold amplitude value. The electrical simulation is output when the peak amplitude value is greater than the threshold amplitude value, and electrical stimulation is triggered without waiting until an epileptic seizure is to be caused by epileptic discharge, which is monitored, which breaks through the limitation that the RNS can only monitor and recognize epileptic discharge and suppress it in a feedback way, and expands the indications of feedback type electrical stimulation treatment to functional brain diseases excluding epilepsy.

Figure 3:
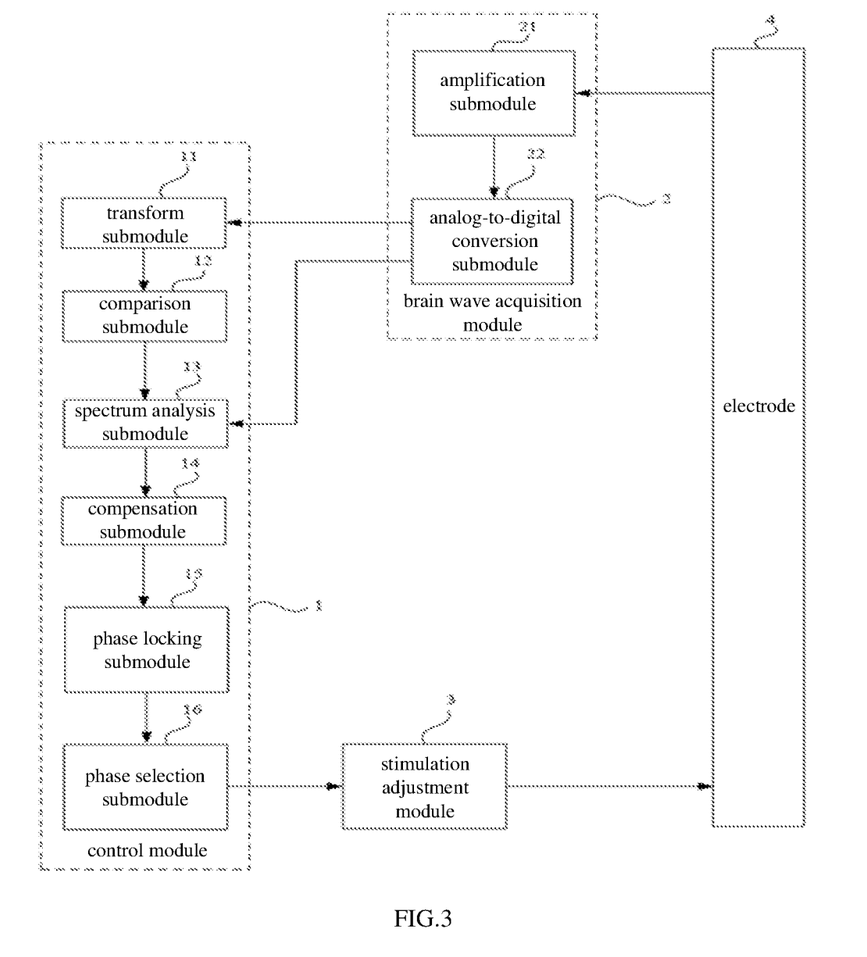
FIG. 3 is a structural schematic diagram of another control module provided by an embodiment of the present invention.

FIG. 3 is a structural schematic diagram of a control module in accordance with another embodiment of the present invention. Based on the electrical stimulation circuit with the structure shown in FIG. 2, the control module 1 may further include compensation submodule 14. The compensation submodule 14 may compensate the brain rhythm phase signals according to acquisition delay parameters and acquire the compensated brain rhythm phase signals.

Specifically, a system delay data table can be used to correct the brain rhythm phase signals, to eliminate time delay caused by acquisition and filter software and achieve accurate phase compensation. In particular, there may be a certain delay between an acquisition process and an acquired signal analysis process, and a new waveform is generated during the analysis of an acquired signal. Therefore, to recover the actual acquired waveform during, an overall finally analyzed waveform can be shifted left. For example, if an acquisition delay parameter can be set to 50 ms, the compensation submodule 14 can left shift the overall waveform corresponding to a brain rhythm phase signal acquired by the spectrum analysis submodule 13 by 50 ms. In this way, the system delay data table is used for correcting the brain rhythm phase signals, which eliminates time delay caused by the acquisition and filter software, achieves accurate phase compensation, and improves the accuracy of the brain rhythm phase signals.

Optionally, with reference to FIGS. 2 and 3, the control module 1 may further include a phase locking submodule 15 and a phase selection submodule 16. The phase locking submodule 15 may perform phase locking on the brain rhythm phase signals and output phase-locked brain rhythm phase signals. The phase selection submodule 16 may select preset waveform phase points in the phase locked brain rhythm phase signals and output stimulation signals at the preset waveform phase points.

Specifically, in some embodiments in which the control module 1 includes the structure shown in FIG. 2, the phase locking submodule 15 performs phase locking on the brain rhythm phase signals output by the spectrum analysis submodule 13, In some embodiments in which the control module 1 includes the structure shown in FIG. 3, the phase locking submodule 15 performs phase locking on the brain rhythm phase signals output by the compensation submodule 14.

Specifically, the brain rhythm phase signals can be subjected to different degrees of phase locking in the key brain region according to different targets. For example, phase locking can be performed at a zero-crossing point of the waveform corresponding to a brain rhythm phase signal or at a preset time after the zero-crossing point of the waveform corresponding to the brain rhythm phase signal. For example, phase locking may be performed for 10s after the zero-crossing point of the waveform corresponding to the brain rhythm phase signal. The phase selection submodule 16 may select a preset waveform phase point in a phase-locked brain rhythm phase signal and outputs a stimulation signal at the preset waveform phase point. That is, the phase selection submodule 16 can implement electrical stimulation at a zero-crossing point of the waveform corresponding to the brain rhythm signals or after phase locking is performed for 10s after the zero-crossing point of the waveform corresponding to the brain rhythm signals. That is, a trigger signal is sent to an electrical stimulation device for phase-coupled stimulation and may perform feedback calculation on the data obtained after stimulation to maintain phase locking of subsequent rhythms.

In this way, by virtue of different electrodes 4, time-locked matching of electrical stimulation of a plurality of targets can be effectively achieved through phase locking of the brain rhythm phase signals. That is, different targets can be stimulated synchronously or sequentially at fixed time intervals, so the problem that the RNS cannot stimulate different targets synchronously or at fixed time intervals is solved.

Optionally, with reference to FIGS. 1-3, each brain wave acquisition module 2 may include an amplification submodule 21 and an analog-to-digital conversion submodule 22. The amplification submodule 21 may acquire brain wave signals on the corresponding electrodes 4 and amplify the brain wave signals to generate amplified brain wave signals. The analog-to-digital conversion submodule 22 may convert the analog amplified brain wave signals into digital amplified brain wave signals and transmitting the amplified brain wave signals to the control module 1.

Specifically, since the brain wave signals at the electrodes 4 are relatively weak, the amplification submodules 21 are configured to amplify the brain wave signals acquired from the corresponding electrodes 4 and convert the amplified brain wave signals in the form of analog signals into amplified brain wave signals in the form of digital signals which can be processed by the control module 1. The accuracy of the processing of the brain wave signals by the control module 1 can be improved by subsequent processing of the amplified brain wave signals in the form of analog signals by the control module 1. For example, each brain wave acquisition module 2 may adopt an ADS1298 chip; the ADS1298 chip has an 8-channel 24-bit delta-sigma synchronous sampling analog-to-digital converter and includes elements such as a programmable gain amplifier, an internal standard unit, and an onboard oscillator. The sampling rate can be set to be 250 Hz.

Optionally, with reference to FIGS. 1-3, the stimulation adjustment modules 3 may adjust voltages of the received stimulation signals and output the voltage-adjusted stimulation signals to the corresponding electrodes 4. Specifically, after receiving the stimulation signals output by the control module 1, the stimulation adjustment modules 3 may adjust the voltages of the stimulation signals output by the control module 1 and output the voltage-adjusted stimulation signals to the corresponding electrodes 4 according to the requirements on electrical stimulation voltages of targets corresponding to the corresponding electrodes 4. For example, each stimulation adjustment module 3 may include a pulse transformer boost circuit.

Optionally, as shown in FIG. 1, the multi-target electrical stimulation circuit may further include a processing module 5. The processing module, for example, may be an MCU (Micro Controller Unit) integrated in the body of a patient. The control module 1, for example, may be a host computer located outside the body of a patient. The processing module 5 may be in wireless communication with the control module 1. The control module 1 may transmit electrical signals containing brain wave stimulation parameters to the processing module 5. Specifically, the control module 1 may be integrated with a first wireless communication submodule. The processing module 5 may be integrated with a second wireless communication submodule. The control module 1 transmits brain wave stimulation parameters to the processing module 5. The wave stimulation parameters may include output polarity, current magnitude, waveform, frequency, and phase of a channel. The processing module 5 controls and adjusts the output stimulation signals accordingly. For example, the processing module 5 may adopt an nRF24LE1 chip that adopts a wireless and ultra-low power consumption technology. A 2.4 GHz wireless transmission and enhanced 51 Flash high-speed single chip is integrated in a 4*4 mm package.

Optionally, as shown in FIG. 1, based on the above embodiment, the multi-target stimulation circuit further includes a wireless charging module 6 and a battery module 7. The wireless charging module 6 may charge the battery module 7 at fixed time intervals. The battery module 7 may supply power to the processing module 5, the brain wave acquisition modules 2, and the stimulation adjustment modules 3.

Specifically, the multi-target stimulation circuit may further include a voltage conversion module 8. The battery module 7 supplies power to the processing module 5. Different voltages are provided to the brain wave acquisition modules 2 and the stimulation adjustment modules 3 through the voltage conversion module 8. The wireless charging module 6 charges the battery module 7 in the body of the patient periodically. The wireless charging module 6 may be in electromagnetic induction with an external power supply 9. The structure in a dashed box in FIG. 1 may be placed in the environment of the patient.

The multi-target stimulation circuit of the embodiment of the present invention includes a plurality of independent stimulation channels and multi-channel brain wave acquisition modules that are entirely isolated electrically from each other. An external host computer wirelessly transmits control parameters and independently adjusts time parameters such as output polarity, current size, waveform, frequency, and phase of each stimulation channel. The multi-target electrical stimulator includes a special processing module and a control module. The processing module includes a microprocessor and a wireless communication module. For example, a host microcomputer achieves communication and is also connected with each independent stimulation channel and brain wave acquisition module through an internal bus system, so that a plurality of targets is stimulated. The overall brain networks of functional brain diseases of a plurality of neural circuits may thus be adjusted. Time-locked matching of electrical stimulation of a plurality of targets is achieved through phase locking of the brain rhythm phase signals.

The embodiments of the present invention further provide a multi-target electrical stimulator that includes the multi-target electrical stimulation circuit described in the above embodiment. Therefore, the multi-target electrical stimulator also has the above beneficial effects, which will not be described in detail here. For example, the multi-target electrical stimulator may include the multi-target electrical stimulation circuit of the above embodiment and may further include a housing for encapsulating the multi-target electrical stimulation circuit and an electrode (i.e., a stimulating probe arranged on the housing and electrically connected with the multi-target electrical stimulation circuit).

Figure 4:
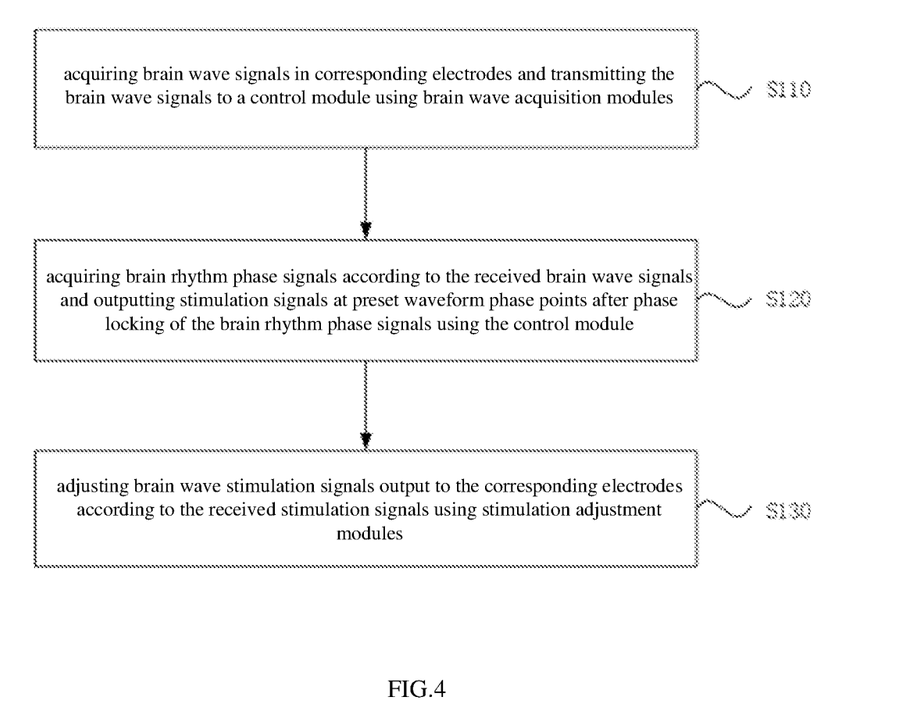
FIG. 4 is a schematic diagram of a flowchart of a signal output method of a multi-target electrical stimulator provided by an embodiment of the present invention.

The embodiment of the present invention further provides a method for outputting signals of a multi-target electrical stimulator. FIG. 4 is a flowchart of the method for outputting signals of the multi-target electrical stimulator in accordance with some embodiments of the present invention. The method for outputting signals of the multi-target electrical stimulator can be implemented by the multi-target electrical stimulator provided by the above embodiments. As shown in FIG. 4, the signal output method of the multi-target electrical stimulator includes:

S110, brain wave signals are acquired from corresponding electrodes and transmitted to a control module by brain wave acquisition modules.

Specifically, referring to FIGS. 1-3, the brain wave acquisition modules 2 may acquire the brain wave signals from the corresponding electrodes 4. That is, the brain wave acquisition modules 2 can monitor brain wave signals at preset positions in the brain in real-time and transmit the brain wave signals to the control module 1. Different electrodes 4 are used for stimulating different targets. Each electrode 4 is associated with a corresponding brain wave acquisition module 2.

S120, brain rhythm phase signals are acquired according to the received brain wave signals and stimulation signals are output at preset waveform phase points after phase locking of the brain rhythm phase signals by the control module.

Specifically, referring to FIGS. 1-3, the control module 1 receives the brain wave signals transmitted by the brain wave acquisition modules 2, acquires the brain rhythm phase signals according to the brain wave signals to realize phase locking of the brain rhythm phase signals, and outputs stimulation signals at the preset waveform phase points of the phase-locked brain rhythm phase signals. For example, phase locking can be performed at or after a zero-crossing point of the brain rhythm phase signals for a preset time. The stimulation signals are then output to phase lock the brain rhythm phase signals. In this way, by virtue of different electrodes 4, time-locked matching of electrical stimulation of a plurality of targets can be effectively achieved by phase locking of the brain rhythm phase signals. That is, different targets can be stimulated synchronously or sequentially at fixed time intervals and may thus solve the problem that different targets cannot be stimulated synchronously or at fixed time intervals.

S130, brain wave stimulation signals output to the corresponding electrodes are adjusted according to the received stimulation signals by the stimulation adjustment modules.

Specifically, each electrode 4 is configured with a corresponding stimulation adjustment module 3.

The embodiment of the present invention is beneficial to achieve stimulation of a plurality of targets, namely stimulation of the key brain regions. Thus, the overall brain networks of functional brain diseases of a plurality of neural circuits are adjusted; the brain wave signals are monitored in real-time to achieve feedback type electrical stimulation adjustment of brain rhythms of a special objective; and time-locked matching of electrical stimulation of a plurality of targets is realized through phase locking of the brain rhythm phase signals, that is, different targets can be stimulated synchronously or sequentially at fixed time intervals.

It should be noted that, related terms such as "first" and "second" herein are merely used for distinguishing one entity or operation from another entity or operation, and do not necessarily require or imply any such actual relationship or order between these entities or operations. Furthermore, the terms "include", "comprise" or any other variation thereof are intended to cover nonexcludable "comprise", so that a process, method, article or device including a series of elements not only includes those elements, but also includes other unclearly listed elements, or further includes inherent elements of this process, method, article or device. Without more restrictions, the elements defined by the sentence "include one . . . " may still mean that there are other identical elements in the process, method, article or device including the elements.

The above descriptions are merely specific embodiments of the present application to make those skilled in the art understand or realize the present application. A variety of modifications of these embodiments will be apparent to those skilled in the art, and the general principles defined herein can be implemented in other embodiments without departing from the spirit or scope of the present application. Therefore, the present application is not limited to these embodiments shown herein but falls within the widest scope consistent with the principles and novel features disclosed herein.

INDUSTRIAL PRACTICABILITY

According to the present invention, the stimulation of a plurality of targets is facilitated, the overall brain networks of functional brain diseases of a plurality of neural circuits are adjusted; the brain wave signals are monitored in real-time to realize feedback type electrical stimulation adjustment of the brain rhythms of a specific objective; and time-locked matching of the electrical stimulation of a plurality of targets is realized through phase locking of the brain rhythm phase signals, so the present invention has a quite high industrial practicability.

The invention claimed is:

1. A multi-target electrical stimulation circuit, comprising:
a control module, a plurality of brain wave acquisition modules, a plurality of electrodes, and a plurality of stimulation adjustment modules, wherein each of the plurality of electrodes is configured with a corresponding brain wave acquisition module and a corresponding stimulation adjustment module, wherein different electrodes are used for stimulating different targets;
wherein the brain wave acquisition modules are configured to acquire brain wave signals in the corresponding electrodes and transmit the brain wave signals to the control module; wherein the control module is configured to obtain brain rhythm phase signals according to the acquired brain wave signals and output stimulation signals at preset waveform phase points after phase locking of the brain rhythm phase signals, wherein the control module comprises:
a transform submodule for performing a Fourier transform on the acquired brain wave signals to obtain amplitude spectra and obtaining peak amplitude values according to the amplitude spectra;
a comparison submodule for comparing the peak amplitude values with threshold amplitude values and adjusting output comparison signals; and
a spectrum analysis submodule configured to perform Fast Fourier Transform (FFT) phase spectrum analysis on the acquired brain wave signals according to the comparison signals to obtain the brain rhythm phase signals; and
wherein the stimulation adjustment modules are configured to adjust brain wave stimulation signals output to the corresponding electrodes according to the stimulation signals.

2. The multi-target electrical stimulation circuit according to claim 1 wherein the control module further comprises:
a compensation submodule for compensating the brain rhythm phase signals according to acquisition delay parameters and obtaining the compensated brain rhythm phase signals.

3. The multi-target electrical stimulation circuit according to claim 1, wherein the control module further comprises:
a phase locking submodule for performing phase locking on the brain rhythm phase signals and outputting phase-locked brain rhythm phase signals; and
a phase selection submodule for selecting the preset waveform phase points in the phase-locked brain rhythm phase signals and outputting the stimulation signals at the preset waveform phase points.

4. The multi-target electrical stimulation circuit according to claim 1, wherein each brain wave acquisition module comprises:
an amplification submodule for acquiring brain wave signals in the corresponding electrodes and amplifying the brain wave signals to generate amplified brain wave signals; and
an analog-to-digital conversion submodule for converting the amplified brain wave signals in the form of analog signals into amplified brain wave signals in the form of digital signals and transmitting the amplified brain wave signals to the control module.

5. The multi-target electrical stimulation circuit according to claim 1, wherein the stimulation adjustment modules are configured to adjust voltages of the stimulation signals and output the voltage-adjusted stimulation signals to the corresponding electrodes.

6. The multi-target electrical stimulation circuit according to claim 1, further comprising:
a processing module in communication connection with the control module and the stimulation adjustment modules, wherein the control module sends the stimulation signals to the stimulation adjustment modules through the processing module.

7. The multi-target electrical stimulation circuit according to claim 6, further comprising:
a wireless charging module and a battery module, wherein the wireless charging module is configured to charge the battery module at preset time intervals, and wherein the battery module is configured to supply power to the processing module, the brain wave acquisition modules, and the stimulation adjustment modules.

8. A multi-target electrical stimulator, comprising a multi-target electrical stimulation circuit that comprises:
a control module, a plurality of brain wave acquisition modules, a plurality of electrodes, and a plurality of stimulation adjustment modules, wherein each electrode of the plurality of electrodes is configured with a corresponding brain wave acquisition module and a corresponding stimulation adjustment module, wherein different electrodes are used for stimulating different targets;
wherein the brain wave acquisition modules are configured to acquire brain wave signals in the corresponding electrodes and transmit the brain wave signals to the control module;
wherein the control module is configured to obtain brain rhythm phase signals according to the acquired brain wave signals and output stimulation signals at preset waveform phase points after phase locking of the brain rhythm phase signals, wherein the control module comprises:
a transform submodule for performing a Fourier transform on the acquired brain wave signals to obtain amplitude spectra and obtaining peak amplitude values according to the amplitude spectra;
a comparison submodule for comparing the peak amplitude values with threshold amplitude values and adjusting output comparison signals; and
a spectrum analysis submodule configured to perform Fast Fourier Transform (FFT) phase spectrum analysis on the acquired brain wave signals according to the comparison signals to obtain the brain rhythm phase signals; and
wherein the stimulation adjustment modules are configured to adjust brain wave stimulation signals output to the corresponding electrodes according to the stimulation signals.

9. A method for output signals for a multi-target electrical stimulator, comprising:
acquiring brain wave signals in corresponding electrodes and transmitting the brain wave signals to a control module by using brain wave acquisition modules, wherein, different electrodes are used for stimulating different targets, and each of the electrodes is configured with a corresponding brain wave acquisition module;
acquiring brain rhythm phase signals according to the acquired brain wave signals and outputting stimulation signals at preset waveform phase points after phase locking of the brain rhythm phase signals by using a control module;
adjusting brain wave stimulation signals output to the corresponding electrodes according to the stimulation signals by using stimulation adjustment modules, wherein each electrode is configured with a corresponding stimulation adjustment module;
performing, by a processor, a Fourier transform on the acquired brain wave signals to obtain amplitude spectra;
obtaining, by the processor, peak amplitude values according to the amplitude spectra;
comparing the peak amplitude values with threshold amplitude values and adjusting output comparison signals; and
performing Fast Fourier Transform (FFT) phase spectrum analysis on the acquired brain wave signals according to the comparison signals to obtain the brain rhythm phase signals.

10. The method of claim 9, further comprising:
compensating the brain rhythm phase signals according to acquisition delay parameters and obtaining the compensated brain rhythm phase signals.

11. The method of claim 9, further comprising:
performing phase locking on the brain rhythm phase signals and outputting phase-locked brain rhythm phase signals; and
selecting the preset waveform phase points in the phase-locked brain rhythm phase signals and outputting the stimulation signals at the preset waveform phase points.

12. The method of claim 9, wherein each brain wave acquisition module comprises:
an amplification submodule for acquiring brain wave signals in the corresponding electrodes and amplifying the brain wave signals to generate amplified brain wave signals; and
an analog-to-digital conversion submodule for converting the amplified brain wave signals in the form of analog signals into amplified brain wave signals in the form of digital signals and transmitting the amplified brain wave signals to the control module.

* * * * *